(12) United States Patent
Solecka et al.

(10) Patent No.: US 8,344,146 B2
(45) Date of Patent: Jan. 1, 2013

(54) INHIBITOR OF DD-PEPTIDASE AND ITS USE AS ANTIBIOTIC OR ANTICANCER DRUG

(75) Inventors: Jolanta Solecka, Warsaw (PL); Lech Kozerski, Warsaw (PL)

(73) Assignee: Narodowy Instytut Zdrowia Publicznego-Panstwowy Zaklad Higieny, Warszawa (PL)

( * ) Notice: Subject to any disclaimer, the term of this patent is extended or adjusted under 35 U.S.C. 154(b) by 232 days.

(21) Appl. No.: 12/675,348

(22) PCT Filed: Aug. 27, 2008

(86) PCT No.: PCT/PL2008/050013
§ 371 (c)(1),
(2), (4) Date: Jul. 26, 2010

(87) PCT Pub. No.: WO2009/028972
PCT Pub. Date: Mar. 5, 2009

(65) Prior Publication Data
US 2010/0286196 A1  Nov. 11, 2010

(30) Foreign Application Priority Data
Aug. 28, 2007  (PL) .......................... 383211

(51) Int. Cl.
*C07D 213/00* (2006.01)
*A61K 31/47* (2006.01)
(52) U.S. Cl. ........................ 546/155; 514/312
(58) Field of Classification Search ............ None
See application file for complete search history.

(56) References Cited

OTHER PUBLICATIONS

Vippagunta, S et al Adv. Drug Deliv. Rev..2001, vol. 48, pp. 15-18.*
Iwasa K. et al., "Simple isoquinoline and benzylisoquinoline alkaloids as potential antimicrobial, antimalarial, cytotoxic, and anti-HIV agents", Bioorganic & Medicinal Chemistry, Elsevier Science Ltd, GB, vol. 9, (Jan. 2001) pp. 2571-2884.
Solecka et al., "P778 A novel not beta-lactam inhibitor of DD-peptidase 64-575", International Journal of Antimicrobial Agents, Elsevier Science, Amsterdam, NL, vol. 29, (Mar. 2007), p. S194.
International Search Report issued by the International Searching Authority (ISA/EP) on Apr. 2, 2009 in connection with International Application No. PCT/PL2008/050013.

* cited by examiner

*Primary Examiner* — Janet Andres
*Assistant Examiner* — Heidi Reese
(74) *Attorney, Agent, or Firm* — Gary J. Gershik; Cooper & Dunham LLP

(57) ABSTRACT

A new compound is revealed and the strain of *Streptomyces* sp. producing it, which may be used in the production of drugs (Formula I).

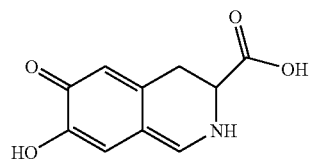

9 Claims, 2 Drawing Sheets

INHIBITOR OF DD-PEPTIDASE AND ITS USE AS ANTIBIOTIC OR ANTICANCER DRUG

This application is a §371 national stage of PCT International Application No. PCT/PL2008/05013, filed Aug. 27, 2008, and claims priority of Polish Patent Application No. P.383211, filed Aug. 28, 2007, the contents of all of which are hereby incorporated by reference into this application.

Due to the increasing resistance of microbes to chemotherapeutics used to date, a real need exists for seeking new antibiotics with alternative chemical structures. β-lactamate based antibiotics constitute a group of compounds most commonly used against bacterial diseases. This is connected with their wide spectrum of activity and a lack of chemoreceptors in Eucaryotae. An extracellular DD-carboxypeptidase/transpeptidase 64-575 II (DD-peptidase 64-575 II) was used in the research. DD-peptidases participate in the final stage of bacterial cell wall synthesis and also bind β-lactamate antibiotics. Enzymes conjugated with an antibiotics lose their catalytic activity, which leads to death in bacteria due to inhibited cell wall synthesis.

The goal of the present invention is to deliver new active compound which, being inhibitors of DD-peptidases, can be used in the production of novel pharmaceutical preparations, in particular antibiotics or cancer drugs. The next goal of the present invention is to deliver a facile method of obtaining such compounds.

Unexpectedly, this goal was attained in the present invention.

The subject of the present invention is a compound with the formula:

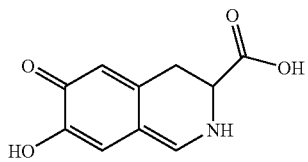 [SMILES: O=C1C=C2CC(C(=O)O)NC=C2C=C1O]

or its pharmaceutically permissible derivative, particularly a salt or a hydrate.

Preferentially, a compound according to the present invention is 7-hydroxy-6-oxo-2,3,4,6-tetrahydroisochinolin-3-carboxylic acid.

The next subject of the present invention is the use of compounds according to the present invention defined above in the production of a drug. Preferentially, the drug produced is an antibiotic or an anticancer drug.

The next subject of the present invention is the use of a *Streptomyces* sp. deposited at the PCM under the accession B/00017 in the production of a compound according to the present invention.

The determination of the structure of a novel active compound which inhibits DD-peptidase activity and which exhibits stability against β-lactamase activity and antibiotic activity can be very significant for antibiotic therapy.

Figure 1:
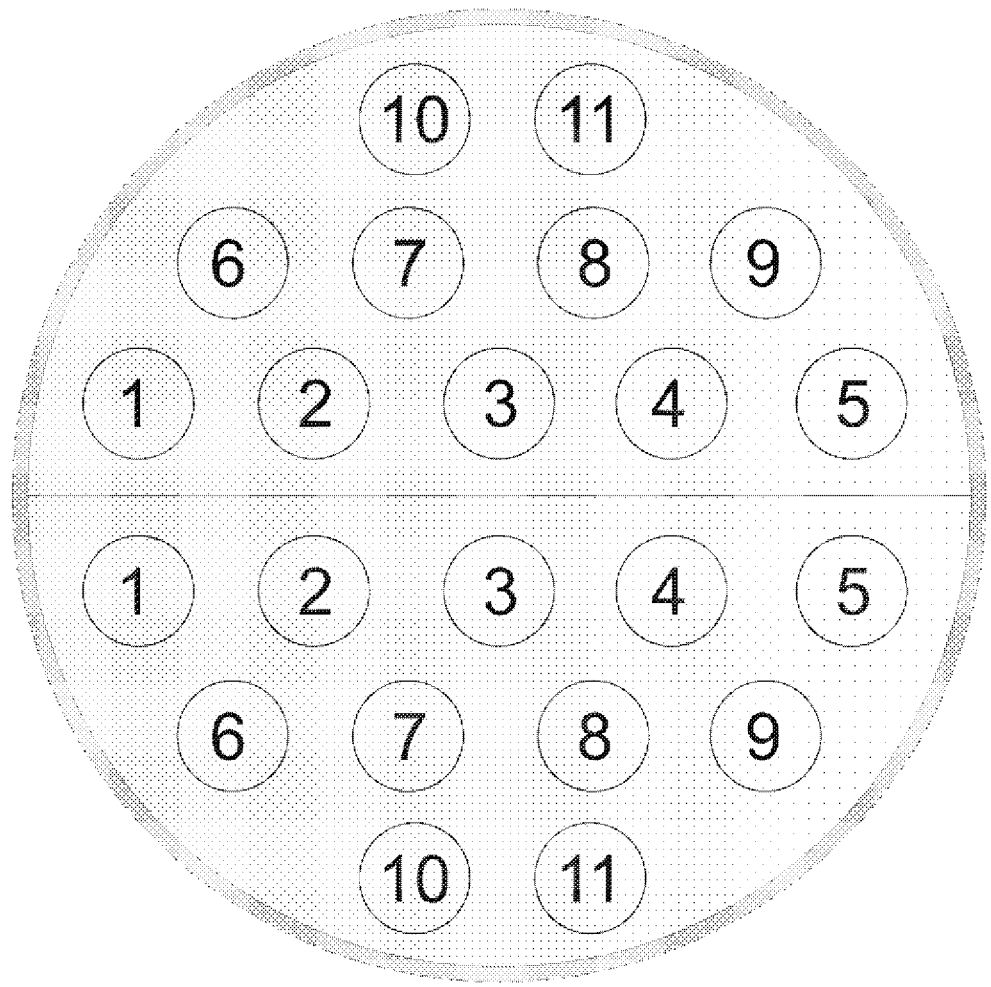
Figure 2:
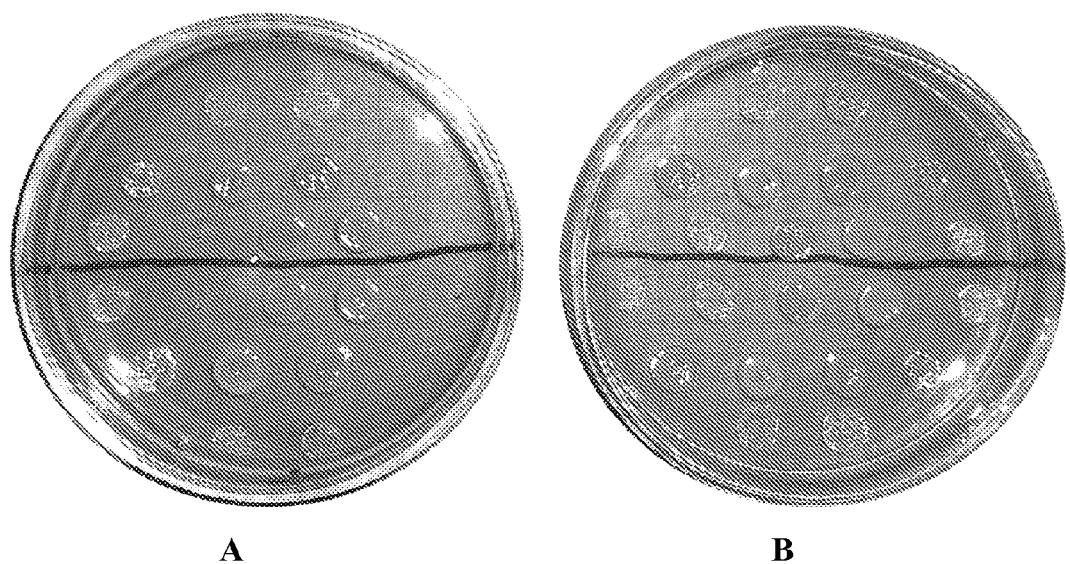

FIG. 1 shows a pattern of bacterial suspensions transferred onto a plate, whereas FIG. 2 shows the result of a test of an antibacterial antibiotic substance according to the present invention at 0.2 mg/ml of medium: A—test sample; B—control sample (lacking the antibiotic substance).

In further portions of the description the authors present detailed examples of embodiments of the presented solution, which are not, however, synonymous with the scope of the present invention defined in the attached Claims.

EXAMPLES

In order to obtain a natural DD-peptidase inhibitor, a compound with antibacterial properties, we cultured *Streptomyces* sp. 8812. This strain was isolated from a soil sample from Brasil. It was deposited in the Polish Collection of Microorganisms (PCM) under accession B/00017.
The following were performed:
1. *Streptomyces* sp. 8812 culture.
2. Purification of the extracellular DD-karboksypeptidase/DD-transpeptidase inhibitor 64-575 II produced by *Streptomyces* sp. 8812.
   a. Deproteination of the culture supernatant
   b. Purification using liquid chromatography in an ion exchange column (IRA-400, Supelco) in a pH gradient.
   c. Purification using standard pressure liquid chromatography in a gradient, in a modified dC18 semi-preparative column, Atlantis (Waters).
   d. Purification using standard pressure liquid chromatography in a gradient, in a modified dC18 analytical column (Atlantis, Waters) (gradient or isocratic method)
   e. Purification using HPLC, analytical dC18 column (Atlantis, Waters)
3. Analyses using HPLC-MS and HR-MS.
4. NMR analysis
5. Determination of the chemical structure of the inhibitor
6. Analysis of the microbiological activity of the inhibitor
7. Use (experimental) of the active compound as a DD-peptidase inhibitor
8. Determination of the inhibitor's characteristics Microbial Culture and Culture Media:
1. Culturing on a Sporulation Medium.

In order to amplify spores of the microbial spores, slants with malt-yeast medium were inoculated with spores of *Streptomyces* sp. 8812 and incubated for 14 days at 28° C.
Composition of the Malt Yeast Sporulation Medium (g/dm³):

| | |
|---|---|
| Yeast extract (Difco) | 4.0 |
| Malt extract (Difco) | 10.0 |
| Glucose | 4.0 |
| Agar (Difco) | 20.0 |

Excluding glucose, the medium components were dissolved in distilled water, brought to pH 7.3. The glucose was added and then the medium was sterilized at 117° C.
2. Culturing in Liquid, Production Medium.
Composition of the Liquid Medium (g/dm³):

| | |
|---|---|
| Tryptone (Difco) | 17.0 |
| Peptone (Difco) | 4.0 |
| Yeast extract (Difco) | 5.0 |
| Corn mash extract (Cerestar, Italy) | 10.0 |
| Lactose | 10.0 |
| $CaCO_3$ | 3.0 |
| $K_2HPO_4$ | 4.0 |
| $KH_2PO_4$ | 2.0 |
| $MgSO_4 \times 7H_2O$ | 0.5 |

The ingredients were dissolved in tap water, boiled for 10 min., brought to pH 6.7 and filtered. The medium was aliquoted into 500 cm³ flasks at 40 cm³ per flask and sterilized at 121° C. for 30 min.

The culture was carried out in 500 cm³ flasks containing 40 cm³ of liquid medium. The medium was inoculated with 1 cm³ of spore suspension ($10^9$) collected from the slants. The incubation lasted 48 hours at 28° C. on a Series 25 Incubator Shaker (New Brunswick Scientific, Edison, N.J., USA) at 240 rpm. Conidial growth was observed using a Carl-Zeiss Docuval phase contrast microscope (Jena, RFN). Following 20, 24 and 48 hours of incubation, culture samples were collected in order to determine DD-peptidase inhibition.

DD-Peptidase 64-575 II. Inhibition Assay

During the *Streptomyces* sp. 8812 culture and subsequent stages of inhibitor purification we used an enzymatic assay for DD-peptidase 64-575 II inhibition. Using this method, we determined the progress of inhibitor biosynthesis, and also selected the fractions with the highest inhibitory activity (which is directly correlated with the selection of compounds exhibiting the highest antibacterial activity).

Extracellular DD-carboxypeptidase/DD-transpeptidase 64-575 II produced by *Saccharopolyspora erythraea* PZH 64-575 II was obtained from the Independent Laboratory of Deuteromycota and Actinomycetales of the National Department of Hygiene. The enzyme was purified to single-protein purity and its characteristics were determined at the Centre for Protein Engineering and Enzymology Laboratory of the University of Liege.

The specific activity of the enzyme is 50 IU/mg.

DD-carboxypeptidase's 64-575 II activity was determined according to Frère et al. 1976'. The reaction mixture for determining DD-peptidase activity contained 60 mm³ of a solution consisting of 0.05 mg·cm$^{-3}$ flavin-adenine dinucleotide (Sigma) in 0.1 M Tris-HCl, pH 8.0; 10 mm³ of a solution containing 0.05 mg·cm$^{-3}$ POX with 1230 U·mg$^{-1}$ activity (Sigma) in distilled water, 5 mm³ of a solution containing 5 mg·cm$^{-3}$ of o-dianisidine chloride (Sigma) in distilled water, 2 mm³ of a solution containing 11.77 mg·cm$^{-3}$ porcine kidney D-amino-acid oxidase (Sigma) with an activity of 6.7 U·mg$^{-1}$ in 0.1 M Tris-HCl at pH 8.0.

The samples for determining DD-carboxypeptidase activity (a) consisted of: 10 mm³ of 50 μM enzyme solution, 20 mm³ of a solution containing 4.52 mg·cm$^{-3}$ of the tripeptide $N^\alpha$, $N^\epsilon Ac_2$-L-Lys-D-Ala-D-Ala in 0.1 M PBS pH 8.0. Control samples (b) contained 20 mm³ 0.089 mg·cm$^{-3}$ D-alanine (Sigma) in place of the substrate. The blank sample (c) contained 20 mm³ 0.1 M PBS pH 8.0 instead of the substrate. All samples (a), (b), (c) were prepared at 4° C., and then incubated for 30 min. at 37° C., whereafter they were placed for 2 min. in a water bath at 100° C. After cooling, samples (a), (b) and (c) were supplemented with 77 mm³ of the reaction buffer, and then incubated for 10 min. at 37° C. Each sample was supplemented with 0.350 cm³ of a mixture containing methanol, distilled water and sulphuric acid at a volume ratio of 5:5:6. Extinction was measured spectrophotometrically at 540 nm on a Spekol 11 spectrophotometer (Carl Zeis Jena, RFN). The amounts of released D-Ala were determined from a calibration curve.

DD-Peptidases 64-575 II Inhibition Analysis:

10 mm³ of a solution of DD-peptidases 64-575 II (50 μM) and 10 (20) mm³ of a purified inhibitor solution were incubated for 30 min. at 37° C. 20 mm³ of substrate (tripeptide) solution were then added and further procedure was performed as described above.

The absorbance of the enzyme control sample ($A_{en}$) was 0.350-0.370, whereas inhibitor sample absorbances ($A_{pr}$) were 0.05-0.10. The inhibition value was determined as a % of DD-peptidases activity inhibition. $I[\%]=100\%-(A_{pr} \times 100\%/A_{en})$.

Inhibition assays also made use of extracellular DD-peptidase R39 produced by *Actinomadura* sp. R39 and DD-peptidase R61 produced by *Streptomyces* sp. R61 obtained from Prof. Jean-Maria Ghuysen. The determinations were performed in an analogous manner, using enzymes concentrations of 0.05 mg/ml and 7.5 μg/ml respectively.

Determination of β-Lactamase Inhibitor Activity Using the Nitrocefin Method (O'Callaghan et al. 1972)[2].

reagents used in the assay: 0.1 mM nitrocefin solution containing 0.5 mg nitrocefin (Glaxo), 0.5 cm³ DMSO (Fluka), 9.5 cm³ 0.1 M PBS pH 7.0; class A β-lactamase (penicillinase, Penase, $5\times10^6$ IU/ml, Bacto).

20 mm³ of the examined inhibitor in 0.1 M PBS pH 7.0 were supplemented with 10 mm³ β-lactamase, incubated for 30 min. at 37° C. Next, 30 mm³ of 0.1 mM nitrocefin solution were added, and 430 mm³ of 0.1M PBS pH 7.0. The samples were incubated for 10 min. at 37° C. and evaluated spectrophotometrically at 482 nm. The molar extinction coefficient was 15000 $M^{-1} \cdot cm^{-1}$.

No differences in absorption were observed against the control sample (β-lactamase with nitrocefin). The inhibitor in question did not inhibit class A β-lactamase.

Determination of Inhibitor Stability in a β-Lactamase Environment.

A method of evaluation inhibitor stability was designed using a combination of the above two methods. An initial incubation of the inhibitor with β-lactamase was performed, and then the reagents for determining DD-peptidase activity inhibition were added. The absorbance of the experimental sample was 0.05, whereas for the control sample (DD-peptidase) it was 0.35. It turned out that after incubating with β-lactamase, the inhibitor retains its inhibitory properties against DD-peptidases 64-575 II, meaning that it is stable in a β-lactamase environment. It is not hydrolysed by β-lactamase.

Inhibitor Purification

The First Stage of Purification of DD-Peptidase 64-575 II Inhibitor

Around 10 dm³ of fermentation broth was centrifuged for 60 mm at 8000 RPM. (Model J-21C Centrifuge, Beckman, USA). The supernatant was deproteinated using acetone added to a concentration of 70% and shaken at RT for 1 hour. The precipitated proteins were centrifuged for 5° C. at 8000 RPM. (Model J-21C Centrifuge; Beckman, USA). Next, the acetone was evaporated off on a vacuum dryer (Unipan, Poland). the entire solution was lyophilised for 24 hours (Beta 1-8 Christ, RFN). The lyophilisate was tested for DD-peptidase inhibition.

The Second Stage of Purification of the DD-Peptidase 64-575 II Inhibitor

The deproteinated lyophilisate of the strain 8812 culture supernatant was loaded in aliquots onto (1.7 g in 20 ml water) IRA 400 transformed acetate ion exchange resin (Supelco). The resin was loaded into a 1.5 cm×22 cm column. This research made use of a standard pressure liquid chromatography apparatus, a BioLogic System (Bio-Rad, USA) equipped with a UV-VIS detector and fraction collector. The loaded lyophilisate was washed with distilled water until reaching zero absorbance at 254 nm. The separation was performed in a pH gradient, using a sequence consisting of: 0.5M acetic acid (0.61, fractions 1-77), 1M acetic acid (0.51-fractions 78-117) and 2M acetic acid (0.31, fractions 118-119). 8 ml fractions were collected, which were frozen, lyophilised, and then examined for inhibitory activity. A high inhibitory activity was obtained in fractions of 0.5M and 1M acetic acid, and a low level of inhibition in 2M acetic acid fractions. The separations were performed in multiple, and active fractions were accreted for further purification.

TABLE 1

Determination of DD-carboxypeptidase/DD-transpeptidase 64-575 II inhibitor activity in fractions following separation on the anion Amberlite IRA-400 exchange resin.

| Fraction number | Inhibition [%]* |
|---|---|
| 3, 4, 5 | 13.8 |
| 6, 7, 8 | 19.9 |
| 9, 10, 11 | 25.7 |
| 12, 13, 14 | 51.9 |
| 18, 19, 20 | 49.0 |
| 30, 31, 32 | 27.5 |
| 36, 37, 38 | 42.7 |
| 53, 54, 55 | 56.6 |
| 59, 60, 61 | 60.2 |
| 68, 69, 70 | 9.8 |
| 78, 79, 80 | 19.2 |

*The measurements made use of 0.05 mg of fraction lyophilisates.

The Second Stage of Purification of the DD-Peptidase 64-575 II Inhibitor

The selected fractions, 53-61 (following purification from the anion exchange resin) exhibiting the highest R61 inhibition activity were purified on a semi-preparative HPLC column with a modified reverse phase, dC18 (Atlantis, 10 μm, 1.0 cm×25 cm, Waters) using standard pressure chromatography (Bio-Logic System, Bio Rad), at a wavelength of 214 nm. The column was loaded with 25-30 mg of lyophilisate in 100 μl 0.05% TFA. The DD-peptidase inhibitor purification program was designed on a computer (program BioLogic, Bio-Rad, USA). This method used multiple times. Solvent flow was 4.7 ml/min. 6 ml fractions were collected. The mobile phase was 0.05% TFA (solution A) and 30% acetonitrile with 70% TFA (0.1%) (solution B). We used a combination isocratic-gradient separation: 10 ml solution A, and then a linear gradient from 0% to 19% of solution B in a volume of 175 ml. The fractions collected were lyophilised and examined for inhibitor activity (inhibition of DD-peptidase 64-575 II). Inhibition was observed for several fractions, at various % of solution B. Several inhibitors were likely separated. Maximum inhibition (95-100%) was shown by fractions 13-15, which were eluted from the column with 9-11% of solution B. Fractions 13-15 yielded around 0.5-1.0 mg of the active substance. The separations on the Atlantis column were performed in multiple, and active fractions were retained for further purification.

The Fourth Stage of Purification of DD-Peptidase 64-575 II Inhibitor

Further purification using standard pressure chromatography (Bio-Logic System, Bio Rad) was performed with an analytical column with a modified reverse phase (Atlantis, 5 μm, 4.6 mm×250 mm, Waters), at a wavelength of 214 nm. The column was loaded with 0.2 (0.15) mg of the sample in 50 μl of 0.05% (v/v) TFA. The sample consisted of a lyophilisate of the active fractions 13-15 (eluted at 9-11% solution B) following chromatographic separation in the Atlantis dC18 semipreparative column.

The following eluents were used: solution A-0.05% TFA, solution B-20% acetonitrile with 80% TFA (0.1%). Microgram quantities of the purified inhibitor were obtained, which was eluted from the column at 2% solution B (isocratic elution) after 35.5 min.

The Fifth Stage of Purification of DD-Peptidase 64-575 II Inhibitor

The inhibitor was purified using the procedure described in the fourth stage. The analysis of NMR and MS spectra confirms the complete purification of the inhibitor.

TABLE 2

Yield efficiency of the inhibitor from the initial material.

| Stage | Amount of purified material following each stage | Quantity ratio of the material following each stage of purification into deproteinated lyophilisate [%] |
|---|---|---|
| Fermentation broth | 1148 cm$^3$ | — |
| Culture supernatant | 840 cm$^3$ | — |
| 1. purification stage; deproteinated lyophilisate | 22 g | 100 |
| 2. purification stage; BioLogic, anion exchange resin | 0.15 g | 0.68 |
| 3. purification stage; BioLogic, semiprep. dC$_{18}$ column. | 10 mg | 0.045 |
| 4. purification stage; BioLogic, dC$_{18}$ analytical column | 3 mg | 0.014 |
| 5. purification stage; HPLC dC$_{18}$ column, single inhibitor | 2.0 mg | 0.009 |

Analyses:
1. Determination of Inhibitor Molecular Mass Using Mass Spectrophotometry.

a) HPLC-MS was performed (HPLC-Hewlett Packard 1100, MS-API 365 Turbo Ionspray (PE SCIEX) using an Atlantis dC18 analytical column (Waters). The mobile phase was 0.05% acetic acid and acetonitrile 98:2; flow rate 1 ml/min; loading volume 20 μl; 214 nm wavelength. MS conditions were: declustering potential 20 V, focusing potential 200 V. Negative ion analysis showed a single molecular peak of 208.1 m/z, and 206.1 m/z for positive ion analysis. The calculated molecular mass is 207.1 Da.

b) Fragmentation of the inhibitor was performed (MS/MS) using a API 365 Turbo Ionspray mass spectrograph from PE SCIEX. The following fragments were obtained: 162.2 (a fragment which is evidence of a carboxyl group); 134.1; 116.0; and 59.1 m/z.

c) Accurate mass measurements were performed (HR-MS) of the inhibitor using a Bruker APEX-Q (9.4T) apparatus and the ESI ionisation method in positive ion analysis. The conditions used were: needle voltage was 3500 V, shield voltage was 3000 V, needle temperature was 200° C. The sample was dissolved in an acetic acid/methanol solution. External calibration was used.

The proposed summary formula resulting from accurate mass measurements is as follows: molecular ion mass $(M+H)^+$ is 208.06040 m/z, whereas the calculated mass is 208.06043 m/z. The computer software package suggested the following inhibitor formula: $C_{10}H_{10}NO_4$ (for m/z). Thus the following summary formula may be proposed: $C_{10}H_9NO_4$. The molecular mass of the purified inhibitor is 207.05258 Da.

2. IR Analysis

An IR spectrum was obtained for the inhibitor (Perkin Elmer Spectrum 2000). The sample was prepared by grinding in KBr.

The following peaks were obtained: 3436 cm$^{-1}$ (hydroxyl group, hydroxyl group from a carboxyl group); 1681 cm$^{-1}$, 1636 cm$^{-1}$ (—C=C—N—, —C=C—O—); 1075 cm$^{-1}$, 1131 cm$^{-1}$ (—C—O—H), 724 cm$^{-1}$, 804 cm$^{-1}$, 894 cm$^{-1}$, 986 cm$^{-1}$ (—C=C—).

3. NMR Analysis $^1$H-NMR analysis was performed (400 MHz, Varian) and $^{13}$C NMR (700 MHz,). The samples were dissolved in H$_2$O/D$_2$O, 9:1

$^1$H NMR H$_2$O/D$_2$O (90:10 vol. %) pH 7.4 Na$_2$HPO$_4$ δ, ppm; 103 (dd, $^2$J=17.1, $^3$J=9.3); 3.15 (dd, $^2$J=17.1, $^3$J=7.3): 4.27 (dd, $^3$J=7.3, $^3$J=9.3); 6.42 (s); 6.92 (s); 8.12 (s);

$^{13}$C NMR δ, ppm; 29.2, 55.6, 110.6, 117.1, 117.2, 135.0, 146.6, 159.5, 168.8, 175.1.

Molecular Structure Determination

The Beilstein database (2006 r) contains ca. 640 structures with the summary formula of C$_{10}$H$_9$NO$_4$. NMR spectrum analysis facilitated the determination of the structure of the analysed inhibitor. This is 7-hydroxy-6-oxo-2.3.4.6-tetrahydroisochinolin-3-carboxylic acid.

The compound described is found in neither the Beilstein nor the Chemical Abstracts databases. This compound is a newly discovered structure.

It is biosynthesized by *Streptomyces* sp. 8812 in a liquid medium containing an organic source of carbon and nitrogen.

It exhibits antibacterial properties. Of note is its inhibition of *Stenotrophomonas maltophilia* ATCC 13637 growth, a bacterium which results in many clinical problems (produces 3 kinds of β-lactamases including a class B metalo- β-lactamase).

Analysis of DD-Peptidase R61 and R39 Activity Inhibition by the Purified Inhibitor, an Isoquinoline Alkaloid DD-peptidase inhibition was expressed in terms of the ID50 (M) describing the molar concentration of inhibitor, which inhibits 50% of enzyme activity.

1) The affinity of DD-peptidase R39 to 7-hydroxy-6-oxo-2.3.4.6-tetrahydroisochinolin-3-carboxilic acid in terms of ID50 (M) is ID50 (M)=4.5×10$^{-4}$M.

2) The affinity of DD-peptidase R61 to the inhibitor in question is ID50 (M)=6.75×10$^{-4}$M.

The Life of the Inhibitor-Enzyme Complex was Also Determined.

The incubation was performed from several to several dozen hours of each enzyme and inhibitor (as described above). Next, the reaction mixture was added, and determinations were performed.

1. The life of the inhibitor-DD-peptidase R 39 complex is 3.5 hours.
2. The life of the inhibitor-DD-peptidase R 61 complex is about 33 hours.

The DD-peptidase R61-inhibitor is much more stable than with enzyme R39. The life of the DD-peptidase R61-inhibitor complex is several dozen hours. This is a value close to the durability of the complexes of DD-peptidase with β-lactamate antibiotics. This is of significance to antibacterial activity.

Microbiological Assays

The antibacterial activity of the compound in question was determined using serial dilutions on solid media (MIC value determination) and using the spot-diffusion protocol. Inhibitor fractions purified on an ion-exchange column were studied (exhibiting the highest activity DD-peptidase inhibition in 0.5M acetic acid). Standard bacterial strains used in the analysis:

1. *Enterococcus faecalis* ATCC 29219,
2. *Stenotrophomonas maltophilia* ATCC 13637
3. *Burkholderia cepacia* ATCC 25416
4. *Acinetobacter baumanii* ATCC 19606
5. *Bordetella bronchiseptica* ATCC 4617
6. *Escherichia coli* ATCC 25922
7. *Klebsiella pneumoniae* ATCC 13883
8. *Escherichia coli* NCTC 8196
9. *Proteus vulgaris* NCTC 4635
10. *Staphylococcus aureus* ATCC 6538P
11. *Staphylococcus aureus* NCTC 4163

A Petri dish was loaded with 0.25 ml of the sample in water and topped with MH II agar medium (Muller Hinton II) to 5 ml. The antibiotic concentration was 0.2 mg/ml medium. Additionally, a control without the antibiotic was made containing 5 ml of MH II. Using a densitometer, bacterial suspensions were made in NaCl solution containing 0.5 McF (10$^8$ CFU/ml), and subsequently dilutions thereof were made.

The following dilution series was made:
10$^4$ CFU/ml NaCl for strains 6, 7, 8, 9
10$^5$ CFU/ml Nan for strains 1, 2, 3, 4, 5, 10, 11

After the medium set, 2 μl of bacterial suspension of each strain was inoculated onto the medium yielding 10$^2$ CFU/ml for strains 6, 7, 8, 9 and 10$^3$ CFU/ml for strains 1, 2, 3, 4, 5, 10, 11. Each suspension was loaded onto each plate. the incubation was performed for 16 hours at 35° C.

Inhibitor activity was observed against the following standard strains: *Proteus vulgaris* NCTC 4635, MIC 0.2 mg/ml; *Bordetella bronchiseptica* ATCC 4617, MIC 0.2 mg/ml, *Stenotrophomonas maltophilia* ATCC 13637, MIC 0.2 mg/ml. For the following strains, the MIC of the studied samples was >0.2 mg/ml.

Inhibitor activity was also determined using the spot-diffusion method.

The analysis was performed using: *Proteus vulgaris* NCTC 4635, *Bordetella bronchiseptica* ATCC 4617, *Stenotrophomonas maltophilia* ATCC 13637. 24 bacterial cultures were used to make suspensions containing 0.2 McF, which was then diluted 100-fold. 0.1 ml of such a mixture was then placed on a dish with Muller-Hinton medium. Discs containing the examined inhibitor fractions were placed and incubated at 35° C. The determinations were carried out at 15 and 18 hours.

The following growth inhibition zones were obtained using 0.4 mg inhibitor per disc:

*Proteus vulgaris* NCTC 4635-20 mm (after 15 h), 19 mm (after 18 h);

*Bordetella bronchiseptica* ATCC 4617-19 mm (after 15 h), 19 mm (after 18 h)

*Stenotrophomonas maltophilia* ATCC 13637-16 mm (after 15 h), 15 mm (after 18 h)

Antifungal Activity Analysis

Inhibitor fractions following stage 2 of purification on an anion exchange column were examined, which exhibited high levels of DD-peptidases 64-575 II inhibition activity. A Petri dish with solid Sabourand medium with 4% glucose was inoculated with a *Candida albicans* ATCC 10231 suspension, at 0.02 McF density. Tissue discs soaked in the inhibitor solution were then placed on the medium (1 mg). The incubation was performed at 35° C. for 24 h. The inhibitor does not exhibit antifungal activity against *Candida albicans* ATCC 10231.

Inhibitor Characteristics.

1.) Solid yellow in colour.
2.) Solubility. The inhibitor is soluble in PBS pH 7.2-8.0; soluble in an aqueous environment with low levels of K$^+$, Na$^+$. It also dissolves in methanol, DMSO, but degrades in these solvents. It is not soluble in ethyl acetate, methylene chloride, chloroform, amyl acetate nor acetonitrile.
3.) Inhibitor stability in the presence of class A β-lactamase: after 24 h incubation in β-lactamase at room temperature, its inhibitory activity of DD-peptidase was completely stable.

LITERATURE

1.) Frère J.-M., et al. Exocellular DD-carboxypeptidases-transpeptidases from *Streptomyces*. Methods Enzymol., 1976, 45, 610-636.
2.) O'Callaghan C. H., et al Novel method for detection of β-lactamase by using a chromogenic cephalosporin substrate. Antimicrob. Agents Chemother., 1972, 1, 283-288.

The invention claimed is:
1. A compound with the formula:

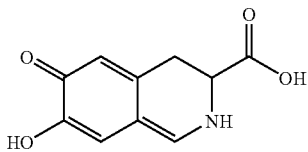 [SMILES: O=C1C=C2CC(C(=O)O)NC=C2C=C1O]

or its pharmaceutically permissible salt.

2. The compound according to claim 1, which is 7-hydroxy-6-oxo-2.3.4.6-tetrahydroisochinolin-3-carboxylic acid.

3. A pharmaceutical composition comprising a carrier and the compound according to claim 1.

4. A process of preparing the compound of claim 1 comprising culturing a strain of *Streptomyces* sp, deposited at the PCM under the accession number B/00017 to produce a broth and isolating the compound from the broth.

5. A process of preparing the compound of claim 2 comprising culturing a strain of *Streptomyces* sp, deposited at the PCM under the accession number B/00017 to produce a broth and isolating the compound from the broth.

6. A method of inhibiting DD-peptidase comprising contacting DD-peptidase with the compound of claim 1.

7. A method of inhibiting DD-peptidase comprising contacting DD-peptidase with the compound of claim 2.

8. A pharmaceutical composition comprising a carrier and the compound according to claim 2.

9. A isolated compound with the formula:

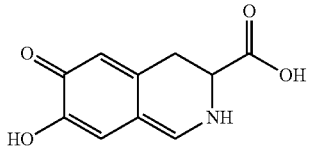

or its pharmaceutically permissible salt.

* * * * *